US00PP34758P2

(12) United States Plant Patent
Post

(10) Patent No.: US PP34,758 P2
(45) Date of Patent: Nov. 22, 2022

(54) ***CHRYSANTHEMUM* PLANT NAMED 'DLFBERI1'**

(50) Latin Name: ***Chrysanthemum* X *morifolium***
Varietal Denomination: 'DLFBERI1'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/833,663

(22) Filed: Jun. 6, 2022

Related U.S. Application Data

(60) Provisional application No. 63/197,948, filed on Jun. 7, 2021.

(51) Int. Cl.
*A01H 5/02* (2018.01)
*A01H 6/14* (2018.01)

(52) U.S. Cl.
USPC ..... Plt./294
CPC ..... *A01H 6/1424* (2018.05)

(58) Field of Classification Search
USPC ..... Plt./294
CPC ..... A01H 5/02
See application file for complete search history.

(56) References Cited

PUBLICATIONS

CPVO Application Consultation 4.1.77 Citation for 'DLFBERI1'; Jun. 15, 2022; 1 page.*

* cited by examiner

*Primary Examiner* — Kent L Bell
(74) *Attorney, Agent, or Firm* — C. Anne Whealy

(57) ABSTRACT

A new and distinct cultivar of *Chrysanthemum* plant named 'DLFBERI1', characterized by its upright plant habit; uniform growth habit; vigorous growth habit and rapid growth rate; durable and robust dark green-colored leaves; strong upright flowering stems; early and freely flowering habit; single-type inflorescences with pure white-colored ray florets and bright green-colored disc florets; relative tolerance to high and low production temperatures; and good post-production longevity.

2 Drawing Sheets

Figure 1:
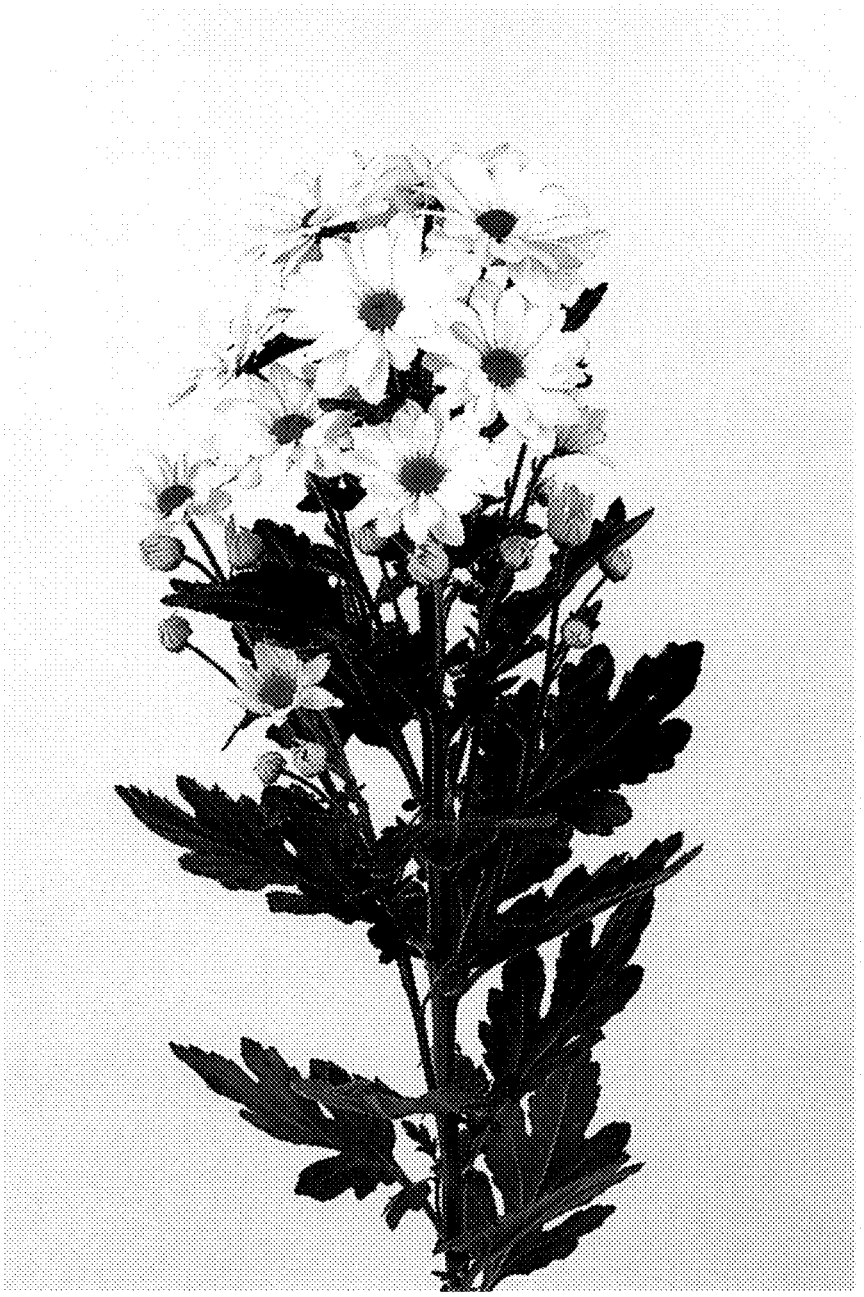

Botanical designation: *Chrysanthemum* X *morifolium*.
Cultivar denomination: 'DLFBERI1'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Jul. 6, 2021, application number A212803. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFBERI1'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in September, 2017 of a proprietary selection of *Chrysanthemum* x *morifolium* identified as code number KR 2015.8291-1, not patented, as the female, or seed, parent with a proprietary selection of *Chrysanthemum* x *morifolium* identified as code number KR 2015.3051-2, not patented, as the male, or pollen, parent. The new *Chrysanthemum* plant was discovered and selected as a single flowering plant from within the progeny of the stated cross-pollination in a controlled greenhouse environment in Maasdijk, The Netherlands in June, 2018.

Asexual reproduction of the new *Chrysanthemum* plant by vegetative terminal cuttings in a controlled greenhouse environment in Maasdijk, The Netherlands since June, 2018 has shown that the unique features of this new *Chrysanthemum* plant are stable and reproduced true to type in successive generations of asexual reproduction.

SUMMARY OF THE INVENTION

The following traits have been repeatedly observed and are determined to be the unique characteristics of 'DLFBERI1'. These characteristics in combination distin guish 'DLFBERI1' as a new and distinct *Chrysanthemum* plant:

1. Upright plant habit; uniform growth habit.
2. Vigorous growth habit and rapid growth rate.
3. Durable and robust dark green-colored leaves.
4. Strong upright flowering stems; early and freely flowering habit.
5. Single-type inflorescences with pure white-colored ray florets and bright green-colored disc florets.
6. Relatively tolerant to high and low production temperatures.
7. Good postproduction longevity.

Plants of the new *Chrysanthemum* differ primarily from plants of the female parent selection in the following characteristics:

1. Leaves of plants of the new *Chrysanthemum* are not as glossy as leaves of plants of the female parent selection.
2. Ray floret apices of plants of the new *Chrysanthemum* are bluntly acute to shallowly praemorse whereas ray floret apices of plants of the female parent selection are mamillate.

Plants of the new *Chrysanthemum* differ primarily from plants of the male parent selection in the following characteristics:

1. Ray floret apices of plants of the new *Chrysanthemum* are bluntly acute to shallowly praemorse whereas ray floret apices of plants of the male parent selection are dentate.
2. At the end of anthesis, disc florets of plants of the new *Chrysanthemum* are yellow green in color whereas disc florets of plants of the male parent selection are light yellow in color.

Plants of the new *Chrysanthemum* can be compared to plants of *Chrysanthemum* X *morifolium* 'DLFARIS1', not patented. In side-by-side comparisons, plants of the new *Chrysanthemum* differ primarily from plants of 'DLFARIS1' in the following characteristics:

1. Leaf sinuses of the new *Chrysanthemum* are deeper than leaf sinuses of plants of 'DLFARIS1'.
2. Ray floret apices of plants of the new *Chrysanthemum* are bluntly acute to shallowly praemorse whereas ray floret apices of plants of 'DLFARIS1' are mamillate.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering stem of 'DLFBERI1' grown as a spray-type cut flower.

Figure 2:
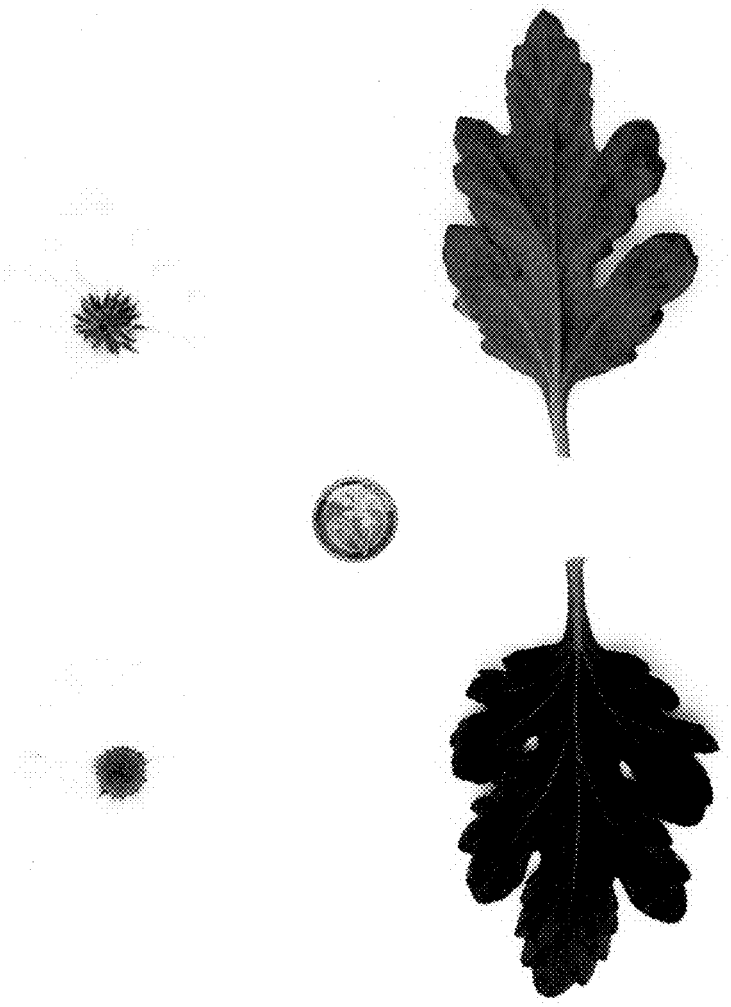

The photograph on the second sheet (FIG. 2) is a close-up view of upper (left) and lower (right) surfaces of typical inflorescences and typical leaves of 'DLFBERI1'.

DETAILED BOTANICAL DESCRIPTION

The aforementioned photographs and following observations and measurements describe plants grown during the early spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFBERI1'.

Parentage:

*Female, or seed, parent*.—Proprietary selection of *Chrysanthemum* x *morifolium* identified as code number KR 2015.8291-1, not patented.

*Male, or pollen, parent*.—Proprietary selection of *Chrysanthemum* x *morifolium* identified as code number KR 2015.3051-2, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 59.1 cm.

*Plant height, soil level to top of inflorescence plane*.—About 71 cm.

*Plant (spray) diameter*.—About 19 cm.

*Flowering stem length*.—About 60.3 cm.

*Flowering stem diameter*.—About 6 mm.

*Flowering stem internode length*.—About 3.1 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143A to 143B.

*Flowering stem color, developed*.—Close to 146B; at the ridges, close to 146B.

*Leaf description*.—Arrangement: Alternate; simple. Length: About 10.3 cm. Width: About 6.5 cm. Shape, in overall outline: Broadly ovate to broadly oblong. Apex: Minutely abruptly acute. Base: Attenuate. Margin: Palmately lobed, coarsely serrate; sinuses convergent and medium to deep in depth; slightly undulate. Texture and luster, upper surface: Moderately pubescent, not rugose; slightly velvety; slightly to moderately glossy. Texture and luster, lower surface: Densely pubescent, not rugose; not velvety; slightly glossy. Venation pattern: Pinnate. Color: Developing leaves, upper surface: Close to a blend of NN137A and 147A. Developing leaves, lower surface: Close to 147B. Fully developed leaves, upper surface: Close to a blend of NN137A and 139A; venation, close to 146C. Fully developed leaves, lower surface: Close to 147B; venation, close to 146C. Petioles: Length: About 1.5 cm. Diameter: About 3 mm by 4 mm. Strength: Moderately strong. Texture and luster, upper surface: Densely pubescent; moderately glossy. Texture and luster, lower surface: Densely pubescent; slightly glossy. Color, upper surface: Close to 146B to 146C; edges, close to NN137A. Color, lower surface: Close to 146C; edges, close to 147B. Stipules: Quantity and appearance: If present, two leafy stipules, opposite, at the petiole attachment to the stem. Length: About 7 mm. Width: About 4.5 mm. Shape: Broadly ovate; apex, short apiculate; base, broadly cuneate; margins, entire. Texture and luster, upper surface: Moderately pubescent; slightly to moderately glossy. Texture and luster, lower surface: Densely pubescent; slightly glossy. Color, upper surface: Close to a blend of NN137A and 139A. Color, lower surface: Close to 147B.

Inflorescence description:

*Appearance*.—Single-type (daisy) inflorescence form with obovate-shaped ray florets and tubular disc florets; inflorescences, rotate in overall shape; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 45 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 13 inflorescences (varying between 11 and 15) develop per flowering stem.

*Inflorescence size*.—Diameter: About 7.3 cm. Depth (height): About 2.6 cm. Disc diameter: About 2 cm.

*Receptacles*.—Height: About 5 mm. Diameter: About 7 mm. Shape: Broadly ovate to broadly deltoid. Color: Close to 145B to 145C.

*Inflorescence buds*.—Height: About 1 cm. Diameter: About 1.2 cm. Shape: Flattened spherical. Texture and luster: Sparsely pubescent; slightly glossy. Color: Developing involucral bracts, close to 137B and 138B; developing ray florets, close to 157A.

*Ray florets*.—Quantity and arrangement: About 25 (varying between 19 and 30) arranged in about two whorls. Length: About 3.1 cm, varying between 2.5 cm and 3.5 cm. Width: About 1.15 cm, varying between 0.8 cm and 1.3 cm. Shape: Obovate; flat to slightly convex or slightly concave; moderately carinate. Apex: Bluntly acute to shallowly praemorse. Base: Cuneate. Margin: Entire; not undulate. Aspect: About 80° from vertical. Texture and luster, upper surface: Smooth, glabrous; moderately velvety; matte. Texture and luster, lower surface: Smooth, glabrous; moderately velvety; slightly glossy. Color: When opening, upper surface: Close to NN155B; towards the base, close to 144C. When opening, lower surface: Close to 157C to 157D; towards the base, close to 144C. Fully opened, upper and lower surfaces: Close to NN155D; towards the base, close to 144B; venation, similar to lamina colors; color does not change with subsequent development.

*Disc florets*.—Quantity and arrangement: About 220 arranged spirally at the center of the receptacle in about ten whorls. Length: About 7 mm. Diameter: About 2 mm. Shape: Tubular; proximally, 85% of the floret is fused. Apex: Acute. Margin, free-part: Entire. Texture and luster, inner and outer surfaces: Smooth, glabrous; glossy. Color, when opening, inner and outer surfaces: Apex: Close to 144C. Mid-section and towards the base: Close to 145C. Color, fully opened, inner and outer surfaces: Apex: Close to 150B. Mid-section and towards the base: Close to a blend of 145C and 150C.

*Involucral bracts*.—Quantity and arrangement: About 24 arranged in about three whorls. Length: About 8 mm. Width: About 4 mm. Shape: Oblong. Apex: Obtuse. Base: Cuneate. Margin: Entire. Texture and luster, upper surface: Smooth, glabrous; glossy. Texture and luster, lower surface: Smooth, glabrous; moderately glossy. Color, upper surface: Close to 143A; lateral margins, translucent and close to 157C and apical margins tinged with close to N199A. Color, lower surface: Close to 137A and 137B; lateral margins, translucent and close to 157C and apical margins tinged with close to N199A.

*Peduncles*.—Length: About 6.3 cm. Diameter: About 3 mm. Strength: Strong. Aspect: Upright. Texture and luster: Moderately pubescent; moderately glossy. Color: Close to a blend of 137B and 143A; at the ridges, close to a blend of 137B and 143A.

*Reproductive organs*.—Androecium: Present on disc florets only. Quantity: About five per floret. Filament length: About 2 mm. Filament color: Close to 154C. Anther size: About 0.5 mm by 1.5 mm. Anther shape: Oblong. Anther color: Close to 3B to 3C. Pollen amount: None observed. Gynoecium: Present on both ray and disc florets. Quantity: One per floret. Pistil length: About 6 mm. Style length: About 5 mm. Style color: Close to 145B. Stigma diameter: About 1 mm. Stigma shape: Cleft, decurrent. Stigma color: Close to 5C. Ovary color: Close to 157D.

*Seeds and fruits*.—To date, seed and fruit development have not been observed on plants of the new *Chrysanthemum*.

Pathogen & pest resistance: Plants of the new *Chrysanthemum* have been observed to be resistant to *Fusarium* (*Fusarium oxysporum* f. sp. *chrysanthemi*). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFBERI1' as illustrated and described.

* * * * *